(12) United States Patent
Vemuri et al.

(10) Patent No.: US 9,168,035 B2
(45) Date of Patent: Oct. 27, 2015

(54) ADJUSTABLE IMPLANT

(75) Inventors: Anand Vemuri, Thousand Oaks, CA (US); Stéphane Gobron, Thousand Oaks, CA (US)

(73) Assignee: Caldera Medical, Inc., Agoura Hills, CA (US)

( * ) Notice: Subject to any disclaimer, the term of this patent is extended or adjusted under 35 U.S.C. 154(b) by 0 days.

(21) Appl. No.: 13/544,916

(22) Filed: Jul. 9, 2012

(65) Prior Publication Data

US 2013/0012765 A1    Jan. 10, 2013

Related U.S. Application Data

(60) Provisional application No. 61/505,494, filed on Jul. 7, 2011, provisional application No. 61/536,984, filed on Sep. 20, 2011.

(51) Int. Cl.
| | |
|---|---|
| A61F 2/02 | (2006.01) |
| A61B 17/04 | (2006.01) |
| A61F 2/00 | (2006.01) |
| A61B 17/00 | (2006.01) |

(52) U.S. Cl.
CPC ........... *A61B 17/0401* (2013.01); *A61F 2/0045* (2013.01); *A61B 17/0469* (2013.01); *A61B 2017/00805* (2013.01); *A61B 2017/0414* (2013.01); *A61B 2017/0456* (2013.01); *A61B 2017/0459* (2013.01); *A61B 2017/0464* (2013.01); *A61F 2250/0007* (2013.01)

(58) Field of Classification Search
CPC .......... A61F 2/0045; A61F 2250/0007; A61B 17/0401; A61B 17/0469; A61B 2017/00805; A61B 2017/0456; A61B 2017/0459; A61B 2017/0464; A61B 2017/0414
USPC .......................... 600/37, 29–31; 128/897–899
See application file for complete search history.

(56) References Cited

U.S. PATENT DOCUMENTS

| | | |
|---|---|---|
| 2003/0130670 A1 | 7/2003 | Anderson et al. |
| 2009/0137862 A1 | 5/2009 | Evans et al. |
| 2010/0069957 A1 | 3/2010 | Abuzaina et al. |
| 2010/0191044 A1 | 7/2010 | Gobron et al. |
| 2010/0191045 A1 | 7/2010 | Gobron et al. |
| 2010/0261950 A1* | 10/2010 | Lund et al. ...................... 600/30 |

FOREIGN PATENT DOCUMENTS

WO    WO 2008/040914 A2    4/2008

OTHER PUBLICATIONS

Machine_Translation_WO2008040914_Houard_NPL.*
WIPO, U.S. International Search Authority, International Search Report and Written Opinion mailed Oct. 16, 2012 in International Patent Application No. PCT/US2012/045986, 9 pages.

* cited by examiner

*Primary Examiner* — Christine H Matthews
*Assistant Examiner* — Sunita Reddy
(74) *Attorney, Agent, or Firm* — Inskeep IP Group, Inc.

(57) ABSTRACT

An implantable support member having at least one adjusting portion operable for adjusting a length or tension of the support member after placement of support member anchors. The support member is operable to provide mid-urethral support for treating urinary incontinence.

11 Claims, 8 Drawing Sheets

Double line ( ⟋ ) indicates portion closest to viewer.

Double line ( ⟋ ) indicates portion closest to viewer.

ADJUSTABLE IMPLANT

RELATED APPLICATIONS

This application claims priority to U.S. Provisional Application Ser. No. 61/505,494 filed Jul. 7, 2011, entitled Adjustable Implant, and U.S. Provisional Application Ser. No. 61/536,984 filed Sep. 20, 2011, entitled Adjustable Implant, both of which are incorporated herein by reference in their entireties.

FIELD OF THE INVENTION

The present invention pertains to the field of medical devices for anchoring and supporting anatomical structures and, more particularly, to implantable slings that are operative to provide support for anatomical structure such as the urethra.

BACKGROUND OF THE INVENTION

There is an estimated 19 million North American adults suffering from urinary incontinence, ranging in severity from partial to complete loss of bladder control. Adults with light incontinence, for example, may experience minimal leakage during the occurrence of a provocative event, such as laughing or coughing, whereas adults with heavy incontinence may experience continuous urine leakage. Moreover, the degree to which an adult is afflicted may change over time.

Generally, urinary incontinence is not considered a disease, but rather a symptom or side effect of another medical condition. For example, female incontinence may be caused by weakened and (or) stretched pelvic muscles, which is associated with child-birth, pregnancy, trauma, prior surgical procedures, and estrogen loss.

Each case of incontinence, however, is unique and no two people are affected by incontinence in the same way. There are, however, well-recognized types of incontinence and various ways to treat the same. Stress incontinence, which is a common type of incontinence, may be characterized as urine leakage during a provocative event such as sneezing, laughing, lifting heavy objects, or when the patient engages in any type of exercise that puts pressure on the bladder. Urge incontinence occurs when the patient wants to urinate but is incapable of exercising restraint until reaching a restroom. Additional types of incontinence include overflow incontinence, which occurs when the quantity of urine exceeds the capacity of the patient's bladder, and functional incontinence, which occurs when the patient has knowledge of the need to urinate but simply cannot access a restroom quickly enough due to a physical obstruction or debilitation.

To treat urinary incontinence, several options are available. The more effective types of recognized treatments include behavioral techniques, such as biofeedback, bladder training, and pelvic muscle exercises, and modifications of the patient's diet and fluid intake. With respect to the latter, it is known that eliminating or cutting back on certain types of substances, such as caffeine and alcohol, can help alleviate incontinence. Additionally, there are medications available, such as dicyclomine (Bentyl), flavoxate (Urispas), hyoscyamine sulfate (Anaspaz), imipramine (Tofranil), oxybutynin (Ditropan), tolterodine (Detrol), and propantheline (Pro-Banthine), phenylpropanolamine (Dexatrim), and pseudoephedrine (Sudafed) that are helpful in controlling urinary incontinence.

Surgery may additionally be an option to treat urinary incontinence. Along these lines, surgical implants are available that provide structural support to the urethra for the treatment of stress incontinence. The implant is operative to provide structural support to the urethra such that during a provocative event, the device will provide structural support to the urethra thus causing the urine to be retained within the bladder and not leak through the urethra. Implants for females, such as the In-Fast Ultra device, produced by American Medical Systems, Inc., of Minneapolis, Minn., is a commercially available surgical implant that may provide structural support to the urethra for the treatment of stress incontinence.

Utilizing these supportive or sling implants to treat incontinence, however, has been known to have numerous drawbacks. Securing suburethral sling implants into position typically requires the use of bone screws, which are well-known in the art to be difficult and time consuming to deploy, and can result in significant patient discomfort, especially within the first couple of weeks following the surgical implantation.

In addition, implanting suburethral slings are often times difficult to secure into position with the optimal degree of tension. Indeed, the implantation of suburethral slings for the treatment of incontinence is well-recognized as complex, time consuming and can produce suboptimal clinical outcomes. Moreover, it is well recognized among surgeons that perform such implant procedures that sutures attached to bone anchors and/or sutures attached to bone screws utilized to secure the sling into position frequently break and that often times additional bone anchors or screws must be secured into position. In fact, each suture attached to bone anchors and or bone screws must typically be re-tensioned two to three times before optimal sling positioning and structural support to the urethra is achieved.

Accordingly, there is a substantial need in the art for a suburethral sling implant for the treatment of incontinence that is substantially easier to surgically secure into position and that can further provide an optimal degree of urethral support to thus effectively treat urinary incontinence. The optimal degree of urethral support varies by patient; therefore, it is desirable that the degree of support provided by the sling implant be adjustable by the surgeon. There is additionally a need in the art for an implant that is of simple construction, easy to surgically manipulate, and can be manufactured at relative low cost utilizing known implant materials, whether it be synthetic materials, natural tissues, or combinations thereof. There is yet a further need in the art for such an implant that can be secured into position such that the implant defines a suburethral sling portion operatively positioned at or distal to the mid-urethral region that remains securely anchored following implantation.

OBJECTS AND SUMMARY OF THE INVENTION

The present invention provides a single-incision implantable solution for mid-urethral support for treating urinary incontinence that advantageously allows intra-operative length or tension adjustment of a support member.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
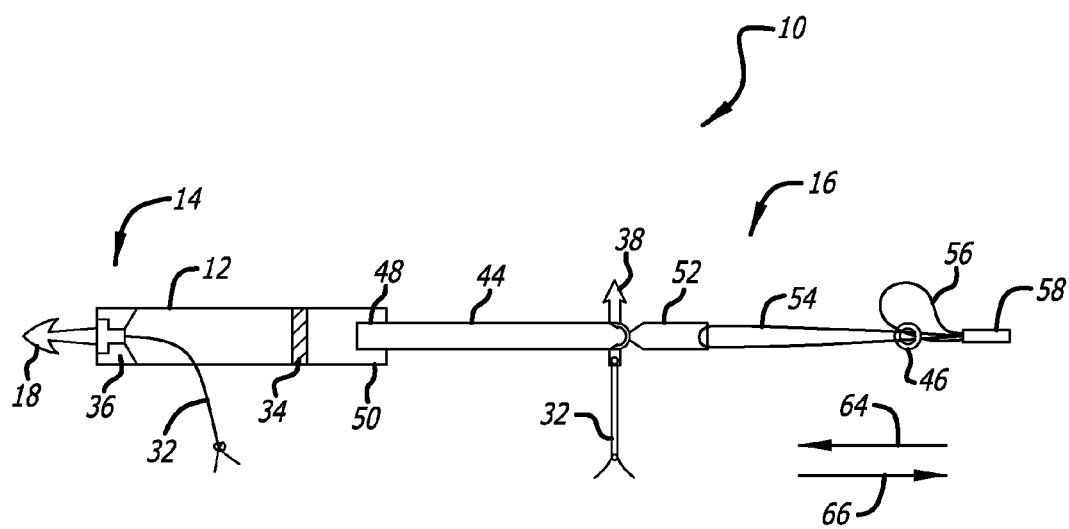
FIG. 1 is a plan view of one embodiment of an implant according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Implants according to the present invention may, for example, be employed to provide single-incision and multi-incision implantable solutions with intra-operative length or tension adjustability to address urinary incontinence through the support of the mid-urethra. More particularly, the present invention provides mid-urethral support that serves to minimize the leakage of urine or incontinence in both male and female patients. Furthermore, implants according to the present invention that employ such intra-operative length or tension adjustability may be alternatively deployed and utilized to address fecal incontinence; pelvic organ prolapse; and other such conditions in both male and female patients.

The implant is advantageously operative to be more easily secured into position than known implants. The implant of the present invention is further capable of being deployed in a manner that is far less traumatic than prior art sling implants and methods of surgically implanting the same, and further utilizes a novel attachment approach that provides for optimal suburethral positioning of the implant.

As shown in FIG. 1, according to one embodiment of the present invention, an implant 10 employs a support member 12 having a fixed portion 14 and an adjustable portion 16.

The support member 12 comprises a material having a generally rectangular or oblong shape. The support member 12 may be fabricated of a synthetic material, such as surgical mesh and the like; natural tissues, such as tissues harvested from either an animal, cadaverous source or the patient himself; and/or combinations of synthetic and natural materials. In one embodiment, the support member 12 is formed of a mesh with knit or weave construction. The strands or fibers forming the mesh of the support member 12 may be oriented parallel to the exterior sides of the support member 12 or may be oriented in a nonparallel fashion relative to the exterior sides of the support member 12. For example, the strands or fibers of the mesh may be oriented at an angle of approximately 45 degrees relative to the exterior sides of the support member 12. The support member 12 may, for example, be 5-30 millimeters wide by 30-150 millimeters long or 8-15 millimeters wide by 50-90 millimeters long.

The support member 12 may further include a position indicator 34 that functions to mark or indicate an approximate reference position of the support member 12 during and after implantation. The indicator 34 may be formed of an ink mark, colored suture or yarn, or other visual and/or physical indicator. In certain embodiments, the position indicator 34 may not be necessary and is omitted entirely.

Figure 2:
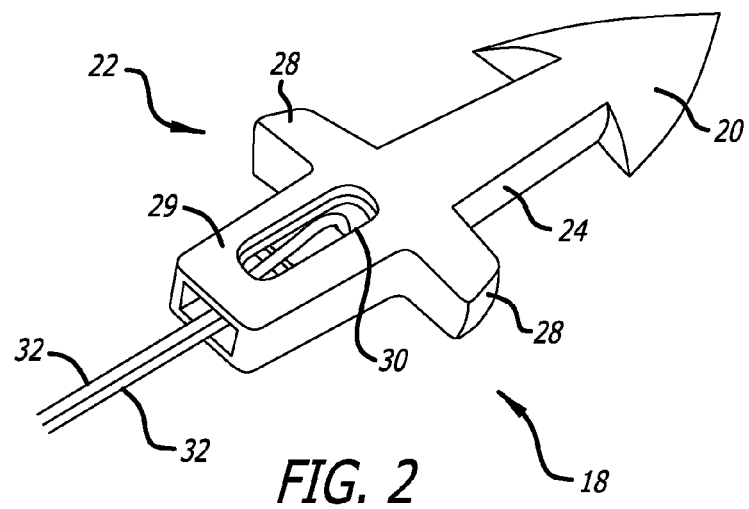
FIG. 2 is a perspective view of one embodiment of an anchor according to the present invention.

The fixed portion 14 of the implant 10 employs an anchor 18. As shown in FIG. 2, the anchor 18 comprises a distal portion 20 and a proximal portion 22 associated with one another by mid-portion 24. As shown in FIGS. 1 and 2, the distal portion 20 may, for example, have an arrowhead-like shape that functions to pierce and secure the distal portion 20 within tissue. The proximal portion 22 of the anchor 18 comprises a shoulder 28 for providing a back-stop for the support member 12 and a guide member 29 for engagement with an anchor delivery system. The proximal portion 22 further employs an aperture or eyelet 30. An anchor suture 32 passes through the eyelet 30 and is, for example, secured back to itself to form a loop. The suture 32 is reversibly or freely slideable in two directions through the eyelet 30. The anchor suture 32 facilitates location and re-engagement of the anchor delivery system with the anchor 18 to which the anchor suture 32 is attached.

Figure 3:
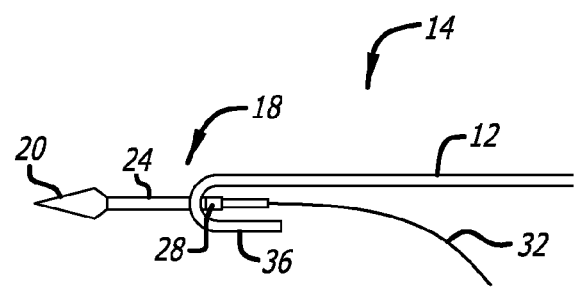
FIG. 3 is a side elevation view of a portion of one embodiment of an implant according to the present invention.

As shown in FIG. 3, the anchor 18 is associated with the fixed portion 14 of the implant 10 by inserting the distal portion 20 of the anchor 18 through the support member 12. In order to assist in securing the anchor 18 to the support member 12, a fold 36 is formed by folding an end portion of the support member 12 back on to itself and bonding, suturing, welding, or tacking to the two portions of the support member 12 to one another so as to maintain the fold.

In certain embodiments, the shoulder 28 of the anchor 18 is omitted. In such embodiments, the support member 12 may be directly attached to the anchor by, for example, using an adhesive, fusing the materials to one another, thermal welding, ultrasonic welding and other technologies operable to achieve a similar resulting attachment of the support member 12 to the anchor 18.

The anchor 18 is employed to pierce a target tissue, such as obturator internus muscle, obturator internus fascia, obturator membrane, arcus tendineus levator ani, and levator ani muscle. The anchor 18 may be formed from a variety of materials, including but not limited to metal alloys, such as titanium, stainless steel, or cobalt-chrome alloys, polymeric materials, such as polyethylene (PE), polypropylene (PP), polysulfone, polyether ether ketone (PEEK), polyether imide (PEI), and biodegradable materials, such as polylactic acid (PLA) and polyglycolic acid (PGA) based materials. The anchor 18 may be formed of a single material or a combination thereof.

Further details regarding the anchor 18 and the attachment of the anchor 18 to the support member 12 are described in the present application's Assignees' U.S. application Ser. Nos. 12/652,640, 12/652,664 and 12/652,706, each of which are incorporated in their entirety by reference. It is noted that in contrast to the implants disclosed in the Assignees' above referenced applications, in view of the adjustable nature of the implant 10 according to the present invention, the ability to re-engage the anchor deployment tool with the anchor may not be necessary or desirable. Hence, in certain embodiments, implants according to the present invention may omit the anchor suture 32 which functions to facilitate re-engagement of the anchor deployment tool with the anchor in order to adjust the anchor or the implant position by manipulating the position of the anchor.

Figure 4:
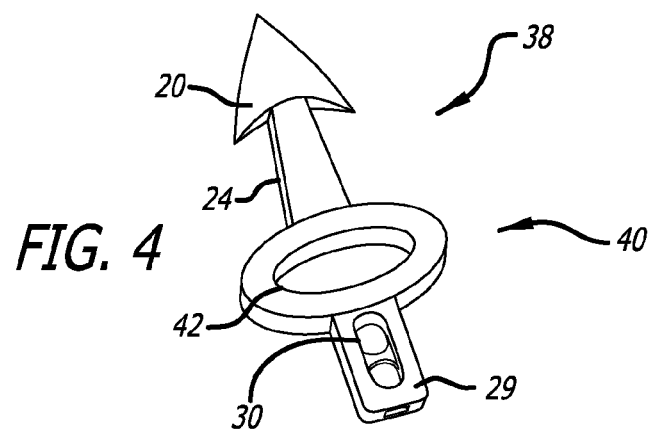
FIG. 4 is a perspective view of one embodiment of an adjustable anchor according to the present invention.

The adjustable portion 16 of the implant 10 employs an adjustable anchor 38 and an adjustable arm 44. As shown in FIG. 4, the adjustable anchor 38 comprises a distal portion 20 and a proximal portion 40 associated with one another by mid-portion 24. The adjustable anchor 38 differs from the anchor 18 in that the proximal portion 40 of the adjustable anchor 38 includes an aperture 42.

A proximal portion 48 of the adjustable arm 44 is attached to an end portion 50 of the support member 12 that is opposite the anchor 18 and fold 36 of the fixed portion 14 of the implant 10. The proximal portion 48 of the adjustable arm 44 may be attached to the distal portion 50 of the support member 12 by adhesive bonding, suturing, ultrasonic welding, thermal welding, radio frequency welding, or tacking the two portions to one another. A distal portion 52 of the adjustable arm 44 is passed through the aperture 42 of the adjustable anchor 38. The adjustable arm 44 is reversibly or freely slideable through the aperture 42. A suture loop 54 is passed through the distal portion 52 of the adjustable arm 44.

Figure 6:
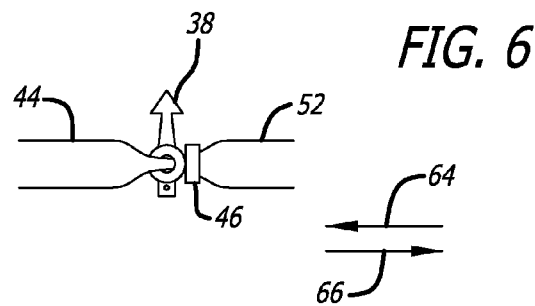
FIG. 6 is a plan view of a portion of one embodiment of an implant according to the present invention.

As shown in FIGS. 1 and 6, the adjustable arm 44 is formed as a separate component from the support member 12. The adjustable arm 44 is formed of a mesh with knit or weave construction having, for example, greater flexibility than the material employed in the support member 12. The greater flexibility may be due to the characteristics of the construction of the mesh, such as the density of threads or fibers used, or may be a characteristic of the material from which the threads or fibers are formed. The threads or fibers forming the mesh of the adjustable arm 44 may be oriented parallel to the exterior sides of the adjustable arm 44 or may be oriented in a nonparallel fashion relative to the exterior sides of the adjustable arm 44. For example, the strands or fibers of the mesh may be oriented at an angle of approximately 45 degrees relative to the exterior sides of the adjustable arm 44.

Figure 5:
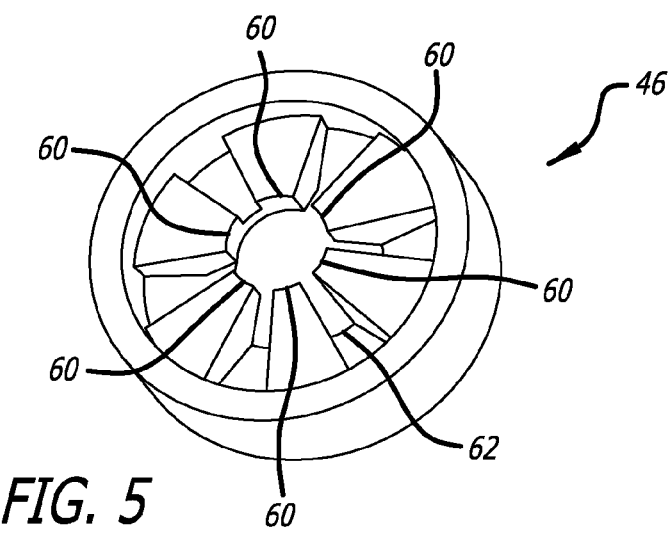
FIG. 5 is a perspective view of one embodiment of a locking member according to the present invention.

The adjustable portion 16 further comprises a locking member 46 through which the suture loop 54 passes. As shown in FIG. 5, the locking member 46 employs an aperture 62 that is defined by one or more engagement members 60 that protrude radially inward. The engagement members 60 may, for example, be formed of a plurality of teeth that project radially inward into the apertures 62. The engagement members 60 provide for one-way movement of the adjustable arm 44 through the aperture 62 in the direction of arrow 64 but lock against movement of the adjustable arm 44 through the aperture 62 in the direction of the arrow 66. The locking member 46 may employ alternative features and methods for providing one-way movement, including any of the embodiments described in the present application's Assignees' U.S. application Ser. No. 12/652,640 (U.S. Pub. No. 2010/0191044; Now abandoned), Ser. No. 12/652,664 (U.S. Pub. No. 2010/0191045; Now U.S. Pat. No. 8,758,220) and Ser. No. 12/652,706 (U.S. Pub. No. 2010/0191046; Now abandoned). The locking member 46 may be formed, for example, of polyethylene (PE), polypropylene (PP), polysulfone, polyether ether ketone (PEEK), polyether imide (PEI), or other suitable polymeric material.

It will be understood that while the locking member 46 and the aperture 62 have been shown as being formed in a generally circular shape, the locking member 46 and the aperture 62 may each be formed in a variety of shapes including rectangular, ovular, and other regular or irregular shapes. The locking member 46 and the aperture 62 need not be formed in the same shape.

In preparation for deployment of the implant 10, the suture loop 54 is passed through the aperture 62. One end of a retaining suture 56 is also passed through the aperture 62. Both ends of the suture loop 54 and both ends of the retaining sutures 56 are secured to one another, as shown in FIG. 1. For example, the ends of the suture loop 54 and the retaining suture 56 may be tied together and/or bound with heat-shrink tubing 58.

For the sake of clarity, it is noted that the locking member 46 is secured relative to the heat-shrink tubing 58 due to one side of the retaining suture 56 being threaded through the locking member 46. Once the retaining suture 56 is cut or otherwise removed, the locking member 46 is freely slideable along a length of the suture loop 54 in one direction. The suture loop 54 functions to guide the adjustment arm 44 through the aperture 62 of the locking member 46 while the retaining suture 56 functions to secure the locking member 46 on the suture loop 54 and thereby to the implant 10. It is noted that the functionalities served by the suture loop 54 and the retaining suture 56 may also be achieved by employing a single suture a first end of which passes through the aperture 62 of the locking member 62, through the distal portion 52 of the adjustable arm 44 and is then looped back and secured to a second, opposite end of the same suture.

A method for deploying or implanting the implant 10 will now be described. First, if not provided completely assembled, the components of the implant 10 are assembled. The assembled implant 10 is shown in FIG. 1. Next, one or more incisions or entry points are made in the patient followed by blunt dissection as necessary and/or desired. The fixed portion 14 of the implant 10 is implanted in, for example the obturator space of the patient, and the adjustable portion 16 of the implant 10 is implanted in, for example the obturator space on the contra-lateral side of the patient. The procedure and deployment tools employed for implanting the anchor 18 and adjustable anchor 38 are identical and described in detail in the present application's Assignees' U.S. application Ser. No. 12/652,640 (U.S. Pub. No. 2010/0191044; Now abandoned), Ser. No. 12/652,664 (U.S. Pub. No. 2010/0191045; Now U.S. Pat. No. 8,758,220) and Ser. No. 12/652,706 (U.S. Pub. No. 2010/0191046; Now abandoned).

Once the anchor 18 and adjustable anchor 38 are implanted within the desired tissue, the physician confirms the desired positioning of the support member 12 and proceeds to tension the support member 12. In order to tension the support member 12, the distal portion 52 of the adjustable arm 44 is pulled to shorten the length of the implant 10 spanning between the patient's anatomy to which the anchor 18 and the adjustable anchor 38 are attached, for example between contra-lateral obturator spaces. Thereby generating an increased tension of the support member 12 beneath the patient's urethra. The distal portion 52 of the adjustable arm 44 can be manipulated to reversibly lengthen or shorten the support member 12 until the desired positioning and length or tension is achieved.

Once the desired length or tension is achieved, the retaining suture 56 securing the locking member 46 is cut. As shown in FIG. 6, the locking member 46 is then slid along the length of the suture loop 54 and the distal portion 52 of the adjustable arm 44 until the locking member 46 contacts the adjustable anchor 38. Since the locking member 46 is sized so as not to pass through the aperture 42 of the adjustable anchor 38 and because the engagement members 60 of the locking member 46 allows only one-way movement of the adjustable arm 44 through the aperture 62, contact of the adjustable anchor 38 and locking member 46 effectively locks the implant 10 at the desired position and tension within the patient. Finally, any excess material and sutures, for example, excess material at the distal portion 52 of the adjustment arm 44 and the sutures 32 and suture loop 54, is trimmed to a safe distance from the locking member 46 and removed.

Figure 7:
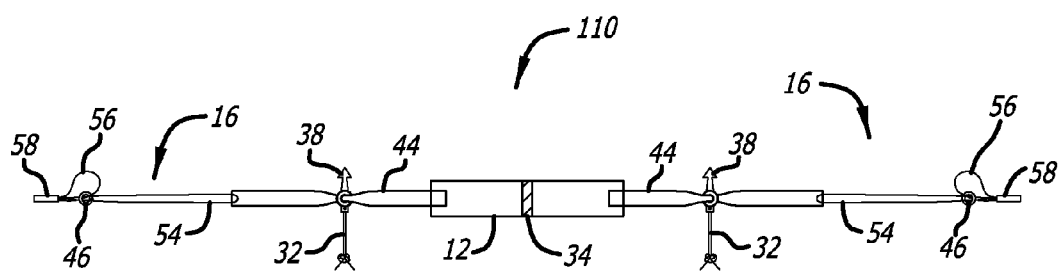
FIG. 7 is a plan view of one embodiment of an implant according to the present invention.

In an alternative embodiment of the present invention, as shown in FIG. 7, an implant 110 employs two adjustable portions 16 positioned at opposite sides of the supporting member 12. In this embodiment, it is noted that the fixed portion 14 is replaced by a second adjustable portion 16. The other components of the implant 110 are as described with respect to the implant 10. The implant 110 provides for increased adjustability of the deployed implant 110.

Figure 8:
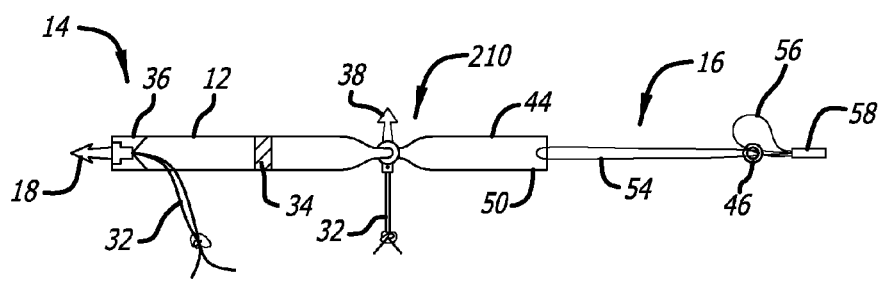
FIG. 8 is a plan view of one embodiment of an implant according to the present invention.

In another embodiment of the present invention, as shown in FIG. 8, an implant 210 has an adjustable arm that is formed of the distal portion 50 of the support member 12. In this embodiment, the adjustable arm 44 and the support member 12 are formed as a single or unitary component and, therefore, need not be attached to one another during assembly of the implant 210. The adjustable arm 44 and the support member 12 may be formed of the same material having the same characteristics throughout or the characteristics of the material may vary between the support member 12 and the adjustable arm 44.

In yet another embodiment of the present invention, the locking member 46 may be incorporated into the aperture 42 of the adjustable anchor 38. Alternatively, the locking member 46 and adjusting arm 44 may be incorporated in to a single component. For example the locking member 46 and adjusting arm 44 may be employed in the form of a zip or cable tie. In such an embodiment, one end of the zip or cable tie is threaded through aperture 42 of the adjustable anchor 38, through the distal portion 50 of the support member and then back through a locking member integrated into the tie.

In an alternative embodiment of the present invention, the adjustable arm 44 is attached to the adjustable anchor 38 and the free end of the adjustable arm 44 is passed through an aperture formed in the distal portion 50 of the support member 12. The free end of the adjustable arm 44 may be locked into place relative to the support member 12 by employing a locking member 46 slideable on the free end of the adjustable arm 44 or by incorporating the locking member 46 into the aperture formed in the distal portion 50 of the support member 12.

The above-described embodiments of the present invention provide significant advantages over known implants. For example, the size of the implant and, more particularly, the degree of support provided by the supporting member, can be customized to patient anatomy. Also, the anchors of the implant can be placed or deployed without simultaneously shortening or tensioning the supporting member, as the shortening or tensioning is achieved in a second independent step.

In embodiments in which the anchor sutures are employed, the anchor deployment tool can be re-engaged with the anchors using the anchor sutures 32. Finally, the adjustable portion of the implant employs a thin, flat strip of material such as a mesh, as opposed to a tubular or other bulky structure that is employed in certain known implants.

Figure 9:
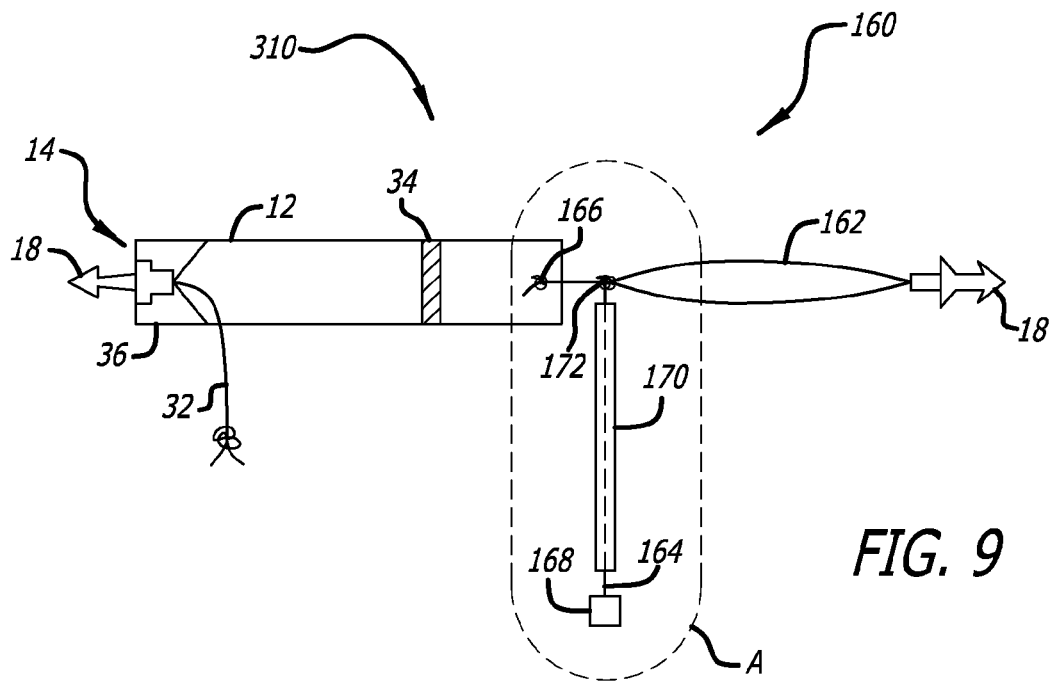
FIG. 9 is a plan view of one embodiment of an implant according to the present invention.
Figure 10:
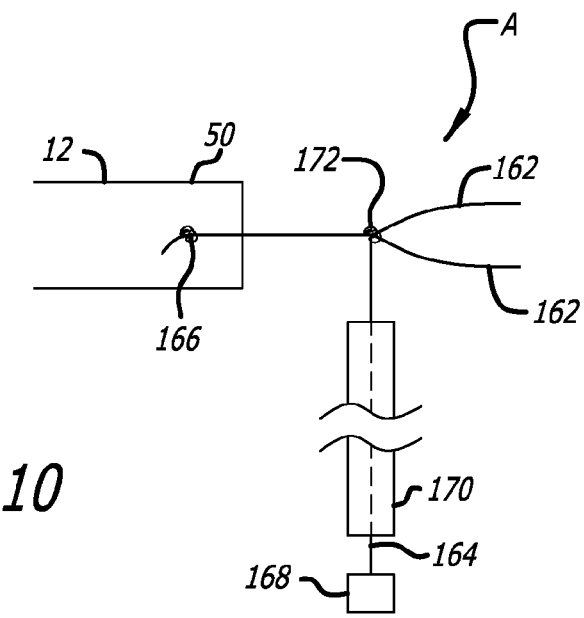
FIG. 10 is a plan view of a portion A of FIG. 9 of one embodiment of an implant according to the present invention.

According to another embodiment of the present invention, as shown in FIGS. 9 and 10, an implant 310 differs from the previously described implants in that the implant 310 employs the adjustable portion 160. The fixed portion 14 and the support member 12 of the implant 310 are as described above.

The adjustable portion 160 employs an anchor 18, an adjusting suture 162, a tube 170, and a sliding locking knot 172. The adjusting suture 162 may be formed, for example, of a monofilament or braided, permanent suture or of a monofilament or braided, absorbable suture. A locking end 166 of the adjusting suture 162 is tied or otherwise attached to the distal portion 50 of the support member 12. The adjusting suture 162 is then passed through the eyelet 30 of the anchor 18, shown in FIG. 2, and tied back to itself to form the sliding locking knot 172 between the locking end 166 of the adjusting suture 162 and the anchor 18. The adjusting suture 162 is reversibly or freely slideable in two directions through the eyelet 30 of the anchor 18. The adjusting portion or post 164 of the adjusting suture 162 is then passed through the tubing 170 and a pull tab 168 is attached to an end of the post 164. The tubing 170 is a flexible tubing that has an internal diameter that is only slightly larger than an external diameter of the adjusting suture 162. The internal diameter of the tubing 170 is smaller than an external diameter of the sliding locking knot 172, i.e. the sliding locking knot 172 will not pass into or through the inner diameter of the tubing 170. It is noted that while the present invention has been described as including the tubing 170 and the pull tab 168, these features are optional and may be omitted and/or replaced while still achieving the desired objective.

Figure 11:
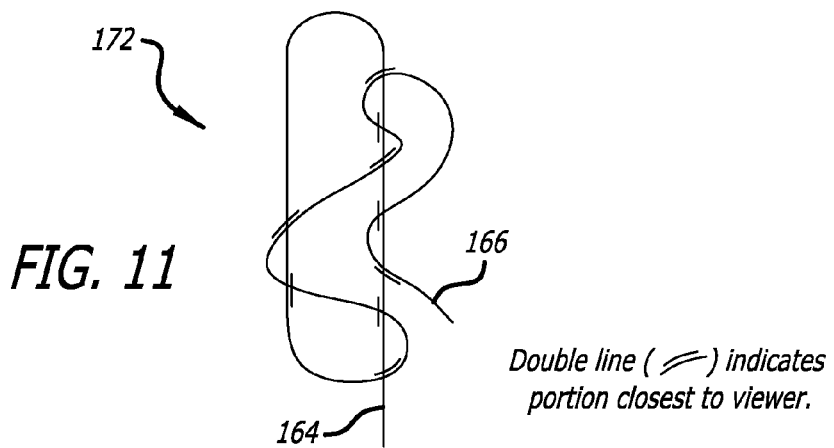
FIG. 11 is a diagram depicting a sliding locking knot employed in one embodiment of an implant according to the present invention.

The sliding locking knot 172 may be formed of a variety of different, known sliding locking knots. For example, the sliding locking knot 172 may be an SMC knot as shown in FIG. 11. It is noted that for the sake of clarity, as shown in FIGS. 11 and 13a-13C, a relatively short parallel line 174 included next to the adjusting suture 162 indicates that the parallel portion of the adjusting suture 162 is on top of or closer to the viewer's eye than the portion of the adjusting suture 162 that is being crossed. Alternative sliding locking knots 172 that may be employed include the Western knot shown in FIG. 13A; the Giant knot shown in FIG. 13B; and the Snyder knot shown in FIG. 13C. A variety of other sliding locking knots may also be employed in the present invention and are described in Baumgarten and Wright, *Arthoscopic Knot Tying,* 2005 which is herein incorporated by reference.

A method for deploying or implanting the implant 310 will now be described. First, if not provided completely assembled, the components of the implant 310 are assembled. The assembled implant 310 is shown in FIG. 9. Next, one or more incisions or entry points are made in the patient followed by blunt dissection as necessary and/or desired. The fixed portion 14 of the implant 310 is implanted in, for example the obturator space of the patient, and the adjustable portion 160 of the implant 310 is implanted in, for example the obturator space on the contra-lateral side of the patient. The procedure and deployment tools employed for implanting the anchors 18 are identical and described in detail in the present application's Assignees' U.S. application Ser. No. 12/652,640 (U.S. Pub. No. 2010/0191044; Now abandoned), Ser. No. 12/652,664 (U.S. Pub. No. 2010/0191045; Now U.S.

Pat. No. 8,758,220) and Ser. No. 12/652,706 (U.S. Pub. No. 2010/0191046; Now abandoned).

Once the anchors 18 are deployed within the desired tissue, the physician confirms the desired positioning of the support member 12 and proceeds to adjust the length or tension of the support member 12. In order to shorten or tension the support member 12, the tubing 170 is held in place to provide counter-tension and the pull tab 168 is pulled. Because the sliding knot 172 does not fit through the interior diameter of the tubing 170, pulling the pull tab 168 effectively shortens the length of adjusting suture 162 between the locking end 166 and the anchor 18 of the adjustable portion 160. That is to say, pulling the pull tab 168 effectively shortens the length of the implant 310 spanning between the patient's anatomy to which the anchors 18 are attached, for example between the patient's contra-lateral obturator spaces, thereby generating an increased tension on the support member 12 beneath the patient's urethra. The sliding locking knot 172 prevents the adjusting suture 162 from backsliding once the pull tab 168 is released. The implant 310 sling is tensioned further until the desired length or tension is achieved.

Once the desired length or tension is achieved, the pull tab 168 is cut or otherwise removed and the tube 170 is removed. The post 164 of the adjusting suture 162 is then trimmed at a safe distance from the sliding locking knot 172.

Figure 12:
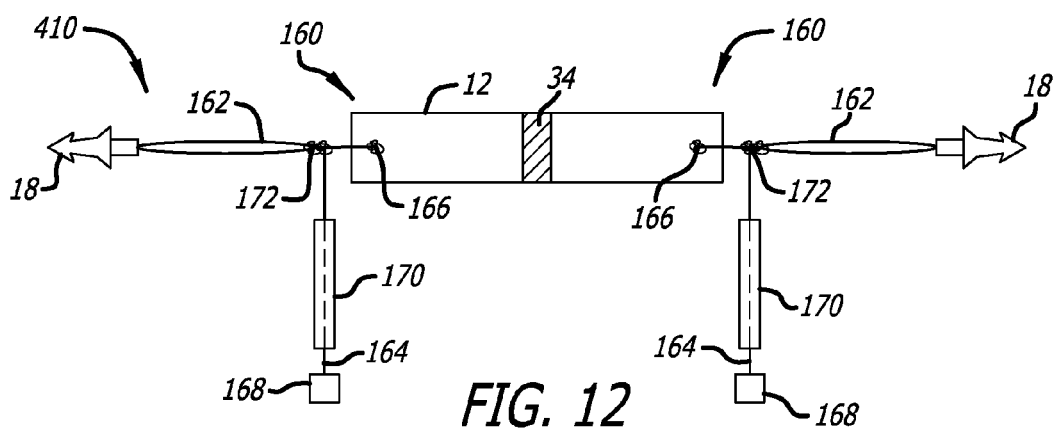
FIG. 12 is a plan view of one embodiment of an implant according to the present invention.
Figure 13A:
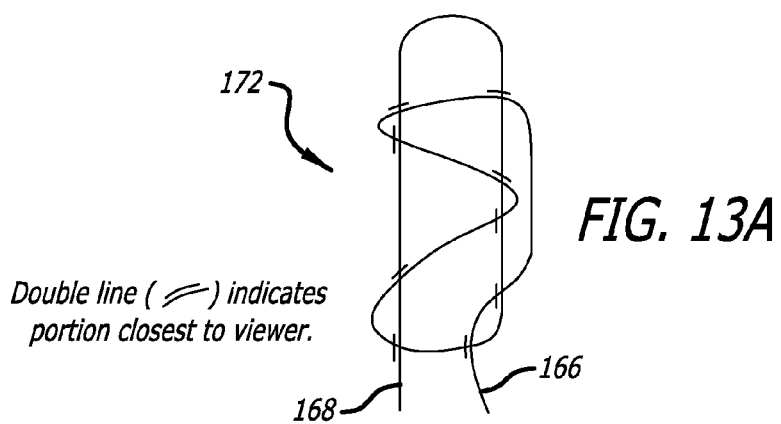
FIGS. 13A-13C is diagrams depicting sliding locking knots employed in implants according to the present invention.
Figure 13B:
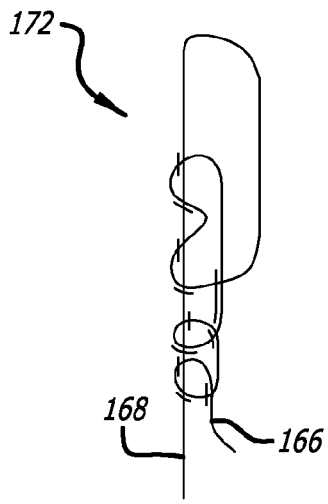
Figure 13B:
Figure 13C:
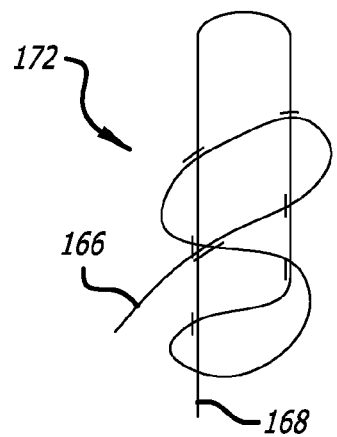
Figure 13C:

In an alternative embodiment of the present invention, as shown in FIG. 12, an implant 410 employs two adjustable portions 160 positioned at opposite sides of the supporting member 12. In this embodiment, it is noted that the fixed portion 14 is replaced by a second adjustable portion 160. The other components of the implant 410 are as described with respect to the implant 310. The implant 410 provides increased adjustability of the deployed implant 410.

Figure 14:
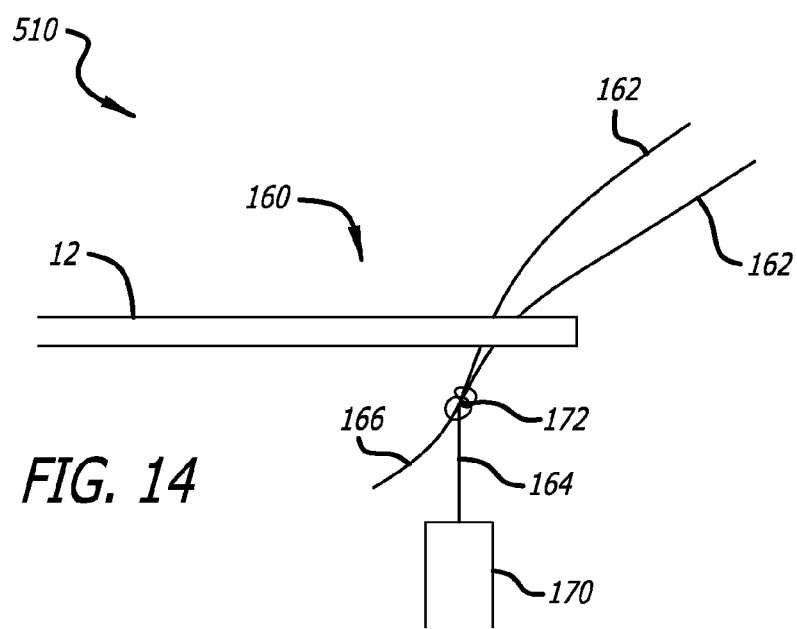
FIG. 14 is a side elevation view of a portion of one embodiment of an implant according to the present invention.

In yet another embodiment of the present invention, as shown in FIG. 14, an implant 510 employs an adjustable portion 160 in which a loop formed by the adjusting suture 162, between the anchor 18, not shown, and the sliding locking knot 172, passes through the support member 12. In contrast to the previously described implants 310 and 410 in which the locking end 166 of the adjusting suture 162 is attached to the supporting member 12, the locking end 166 of the implant 510 remains free. The above-described embodiments of the present invention provide significant advantages over known slings. For example, the size of the implant and, more particularly, the supporting member, can be customized to patient anatomy. Also, the anchors of the implant can be placed or deployed without simultaneously shortening or tensioning the supporting member, as the shortening or tensioning is achieved in a second independent step. In embodiments in which the anchor sutures are employed, the anchor deployment tool can be re-engaged with the anchors using the anchor sutures 32. Furthermore, due to the lower total volume of material employed in the present implant, the implant is less prone to inducing detrimental foreign body responses in the patient. Finally, the implant according to the present invention requires no additional steps to lock the implant after a desired length or tension is achieved.

Figure 15A:
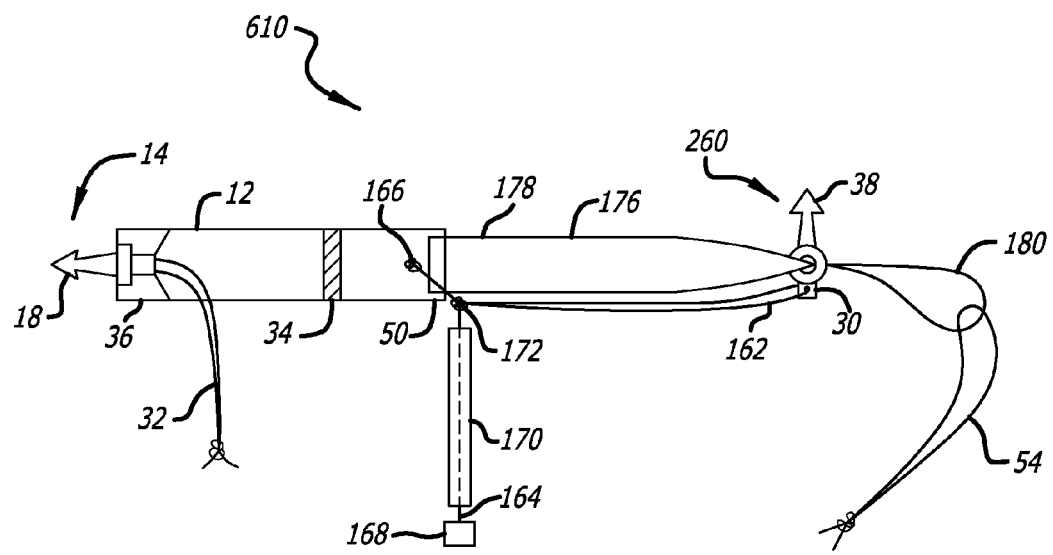
FIG. 15A is a plan view of an implant according to one embodiment of the present invention.
Figure 15B:
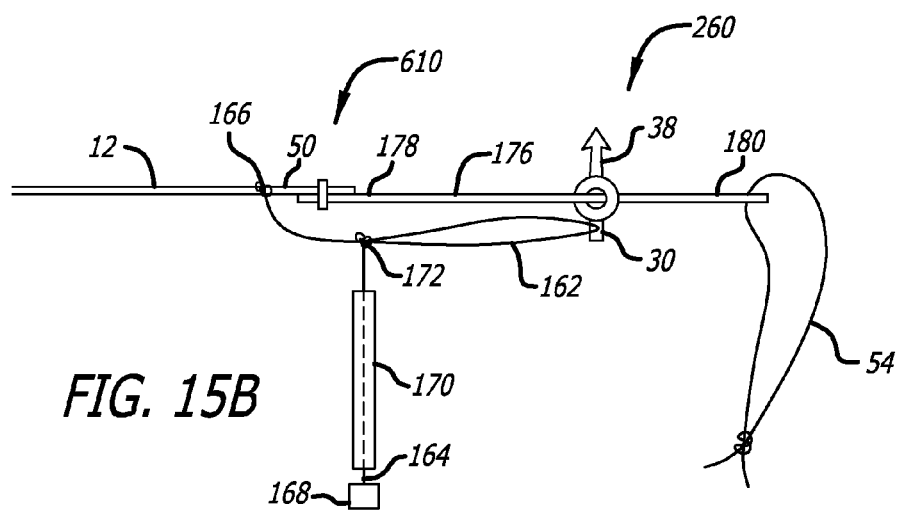
FIG. 15B is a side elevation view of a portion of an implant according to one embodiment of the present invention.

According to another embodiment of the present invention, as shown in FIGS. 15A and 15B, an implant 610 differs from the previously described implants in that the implant 610 employs a sliding arm 176 and an adjustable portion 260. The fixed portion 14 and the support member 12 of the implant 610 are as described above.

The adjustable portion 260 employs the adjustable anchor 38, as described above, and the adjusting suture 162, the tube 170, and the sliding locking knot 172, as also described above. The adjusting suture 162 may be formed, for example, of a monofilament or braided, permanent suture or of a monofilament or braided, delayed absorbable suture. A locking end 166 of the adjusting suture 162 is tied or otherwise attached to the distal portion 50 of the support member 12. The adjusting suture 162 is then passed through the eyelet 30 of the adjustable anchor 38 and tied back to itself to form the sliding locking knot 172 between the locking end 166 of the adjusting suture 162 and the adjustable anchor 38. The adjustable suture 162 is reversibly or freely slideable in two directions through the eyelet 30 of the adjustable anchor 38. The adjusting portion or post 164 of the adjusting suture 162 is then passed through the tubing 170 and a pull tab 168 is attached to an end of the post 164. It is noted that while the present invention has been described as including the tubing 170 and the pull tab 168, these features are optional and may be omitted and/or replaced while still achieving the desired objectives.

The sliding locking knot 172 may be formed of a variety of different, known sliding locking knots. For example, the sliding locking knot 172 may be an SMC knot as shown in FIG. 11. It is noted that for the sake of clarity, as shown in FIGS. 11 and 13a-13C, a relatively short parallel line 174 included next to the adjusting suture 162 indicates that the parallel portion of the adjusting suture 162 is on top of or closer to the viewer's eye than the portion of the adjusting suture 162 that is being crossed. Alternative sliding locking knots 172 that may be employed include the Western knot shown in FIG. 13A; the Giant knot shown in FIG. 13B; and the Snyder knot shown in FIG. 13C. A variety of other sliding locking knots may also be employed in the present invention and are described in Baumgarten and Wright, *Arthoscopic Knot Tying*, 2005 which is herein incorporated by reference.

The implant 610 differs from the implant 310 primarily in that the end portion 50 of the support member 12 that is opposite the fixed portion 14 of the implant 610 is attached to a proximal portion 178 of the sliding arm 176. The proximal portion 178 of the sliding arm 176 may be attached to the distal portion 50 of the support member 12 by adhesive bonding, suturing, ultrasonic welding, thermal welding, radio frequency welding, or tacking the two portions to one another. A distal portion 180 of the sliding arm 176 is passed through the aperture 42 of the adjustable anchor 38. The suture loop 54 is passed through the distal portion 180 of the sliding arm 176.

A method for deploying or implanting the implant 610 will now be described. First, if not provided completely assembled, the components of the implant 610 are assembled. The assembled implant 610 is shown in FIGS. 15A and 15B. Next, one or more incisions or entry points are made in the patient followed by blunt dissection as necessary and/or desired. The fixed portion 14 of the implant 610 is implanted in, for example the obturator space of the patient, and the adjustable portion 260 of the implant 610 is implanted in, for example the obturator space on the contra-lateral side of the patient. The procedure and deployment tools employed for implanting the anchor 18 and adjustable anchor 38 are identical and described in detail in the present application's Assignees' U.S. application Ser. No. 12/652,640 (U.S. Pub. No. 2010/0191044; Now abandoned), Ser. No. 12/652,664 (U.S. Pub. No. 2010/0191045; Now U.S. Pat. No. 8,758,220) and Ser. No. 12/652,706 (U.S. Pub. No. 2010/0191046; Now abandoned).

Once the anchor 18 and adjustable anchor 38 are deployed within the desired tissue, the physician confirms the desired positioning of the support member 12 and proceeds to adjust the tension or length of the support member 12. If desire, the physician may initially reversibly adjust the length or tension by pulling the suture loop 54 attached to the distal portion 180 of the sliding arm 176. In order to fix or lock the length or tension of the support member 12, the tubing 170 is held in place to provide counter-tension and the pull tab 168 is pulled. Because the sliding knot 172 does not fit through the interior diameter of the tubing 170, pulling the pull tab 168 effectively shortens the length of the adjusting suture 162 between the locking end 166 and the adjustable anchor 38 of the adjustable portion 260. That is to say, pulling the pull tab 168 effectively shortens the length of the implant 610 spanning between the patient's anatomy to which the anchors 18 are attached, for example between the patient's contra-lateral obturator spaces, thereby generating an increased tension or decreased length of the support member 12 beneath the patient's urethra. The sliding locking knot 172 prevents the adjusting suture 162 from backsliding once the pull tab 168 is released. The implant 610 is tensioned further until the desired length or tension is achieved.

Once the desired length or tension is achieved, the pull tab 168 is cut or otherwise removed and the tube 170 is removed. The post 164 of the adjusting suture 162 is then trimmed at a safe distance from the sliding locking knot 172. Next, the distal portion 180 of the sliding arm 176 is pulled and/or otherwise manipulated through the aperture 42 of the adjusting anchor 38 to remove any folds or surface irregularities of the sliding arm 176. It is noted that at this stage, the sliding arm 176 should be positioned between adjusting suture 162 and patient tissue. Finally, any excess material and sutures, for example, excess material at the distal portion 180 of the sliding arm 176 and the sutures 32 and suture loop 54, is trimmed as desired and removed.

Figure 16:
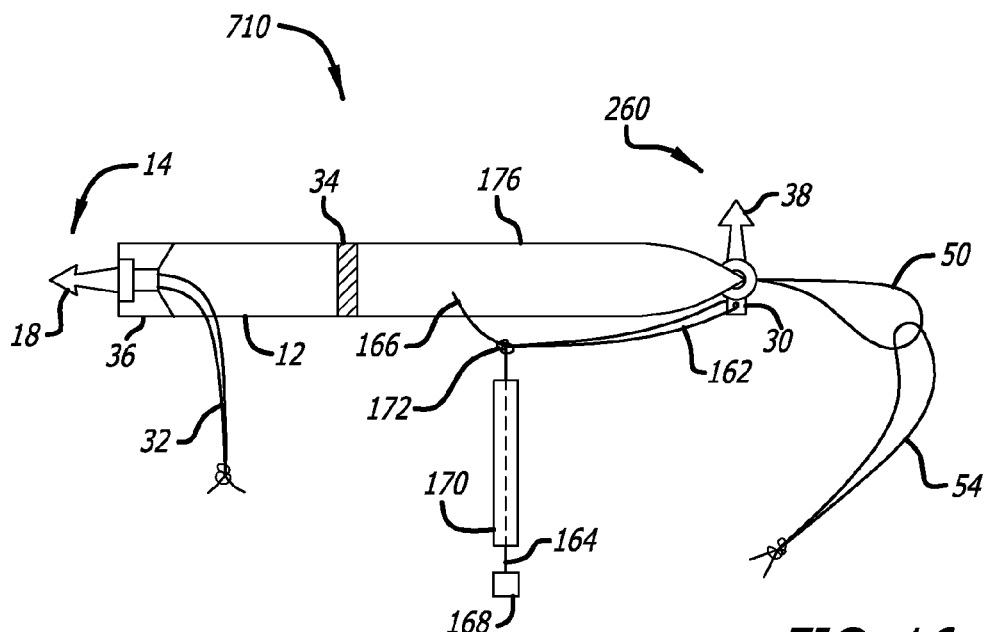
FIG. 16 is a plan view of an implant according to one embodiment of the present invention.

In an another embodiment of the present invention, as shown in FIG. 16, an implant 710 has an sliding arm that is formed of the distal portion 50 of the support member 12. In this embodiment, the sliding arm 176 and the support member 12 are formed as a single component and, therefore, need not be attached to one another during assembly of the implant 710. The sliding arm 176 and the support member 12 may be formed of the same material having the same characteristics throughout or the characteristics of the material may vary between the support member 12 and the sliding arm 176.

Figure 17:
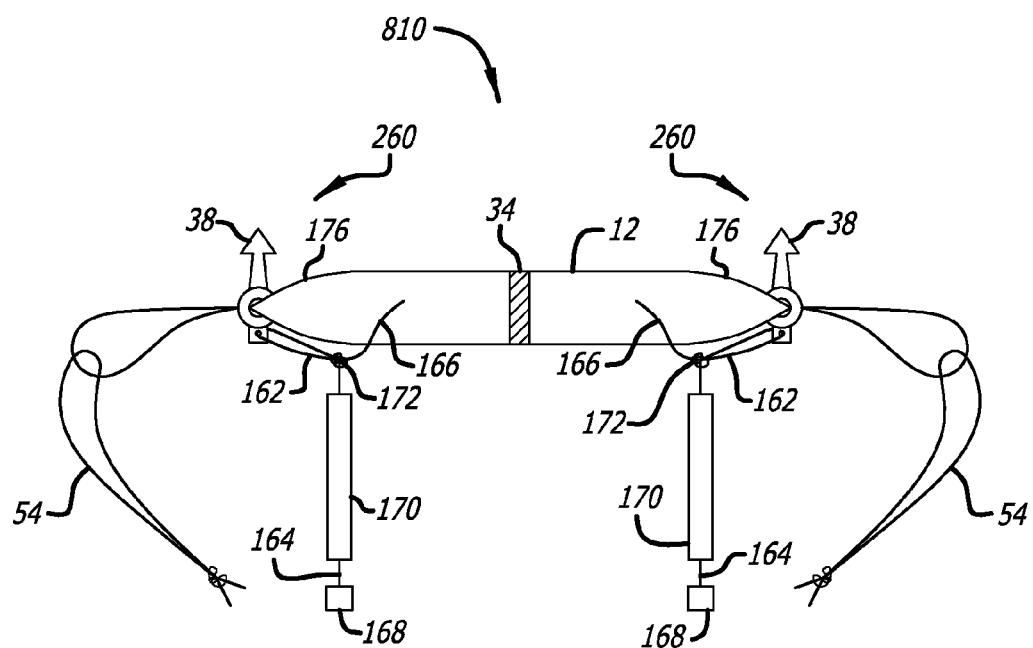
FIG. 17 is a plan view of an implant according to one embodiment of the present invention.

In an alternative embodiment of the present invention, as shown in FIG. 17, an implant 810 employs two adjustable portions 260 positioned at opposite sides of the supporting member 12. In this embodiment, it is noted that the fixed portion 14 described with respect to the implant 610 is replaced by a second adjustable portion 260. The other components of the implant 810 are as described with respect to the implant 610. The sliding arms 176 may be formed as described above with respect to the implant 610 or as described above with respect to the implant 710. The implant 810 provides increased adjustability of the deployed implant over that described for certain of the above-described embodiments.

The above-described embodiments of the present invention provide significant advantages over known slings. For example, the size of the implant and, more particularly, the degree of support of the supporting member, can be customized to patient anatomy. Also, the anchors of the implant can be placed or deployed without simultaneously shortening the length or tensioning the supporting member, as the shortening of length or tensioning is achieved in a second independent step. In embodiments in which the anchor sutures are employed, the anchor deployment tool can be re-engaged with the anchors using the anchor sutures 32. Furthermore, the implant according to the present invention requires no additional steps to lock the implant after a desired length or tension is achieved. Finally, the use of the sliding arm 176 that is ultimately positioned between patient tissue and the adjusting suture 162 functions to provide a platform for tissue ingrowth.

In certain embodiments of the present invention, implants may employ combinations of the above described features of the implants 10, 110, 210, 310, 410, 510, 610, 710 and 810. Furthermore, in certain embodiments of the present invention, implants may employ supporting members having regular and irregular shapes, as well as three or more adjusting arms.

Implants comprising the above described features and variations thereof may be employed in order to treat a variety of conditions, such as urinary incontinence, fecal incontinence, pelvic organ prolapse, and other such conditions in both male and female patients.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An adjustable implant, in an assembled state, comprising:
    a support member formed of mesh;
    a first anchor inserted through the mesh of the support member approximate a first end of the support member;
    an arm formed of mesh and extending from a second end of the support member;
    a second anchor having an aperture through which the mesh of the arm passes; and
    an adjusting suture having a locking end, a looped portion, and an adjusting portion, the locking end of the adjusting suture attached directly to the mesh of the second end of the support member, the looped portion of the adjusting suture passing directly through an eyelet in the second anchor, and a portion of the adjusting portion of the adjusting suture surrounded by a tubing, the adjusting suture having a sliding locking knot formed at an intersection of the locking end, the looped portion, and the adjusting portion of the adjusting suture, the sliding locking knot configured to provide for a reduction in a length between the second end of the support member and the second anchor and to substantially prevent an expansion of said length.

2. The adjustable implant of claim 1 wherein the aperture of the second anchor is configured such that the arm reversibly slides through the aperture.

3. The adjustable implant of claim 1 wherein said arm is unitary with the support member.

4. The adjustable implant of claim 1 wherein the sliding locking knot is positioned between the first and second anchors.

5. An adjustable implant, in an assembled state, comprising:
    a support member formed of mesh;
    a first anchor inserted through the mesh of the support member approximate a first end of the support member;
    an adjusting suture having a locking end, a looped portion, and an adjusting portion, the locking end of the adjusting suture attached directly to the mesh of a second end of the support member;
    a second anchor having an eyelet through which a looped portion of the adjusting suture passes; and a sliding locking knot formed at an intersection of the locking end, the looped portion, and an adjusting portion of the adjusting suture, the sliding locking knot configured to allow a reduction in size of the looped portion of the adjusting suture and to substantially prevent an expansion in size of the looped portion of the adjusting suture; and a tubing surrounding a portion of the adjusting portion of the adjusting suture.

6. The adjustable implant of claim 5 wherein the adjusting suture is reversibly slideable through the eyelet of the second anchor.

7. The adjustable implant of claim 5 wherein the sliding locking knot comprises a knot selected from a group consisting of: an SMC knot, a Western knot, a Giant knot, and a Snyder knot.

8. The adjustable implant of claim 5 further comprising a tab attached to an end of the adjusting portion of the adjusting suture.

9. The adjustable implant of claim 5 wherein the support member comprises an arm extending from the second end of the support member.

10. The adjustable implant of claim 9 wherein said arm is unitary with the support member.

11. The adjustable implant of claim 9 wherein the second anchor comprises an aperture reversibly slideable over the arm.

* * * * *